United States Patent [19]

Karsanov et al.

[11] Patent Number: 5,602,105
[45] Date of Patent: Feb. 11, 1997

[54] CARDIOTROPIC FORMULATION

[76] Inventors: Nikolai V. Karsanov, ulitsa Gotua, 16, kv. 96, Tbilisi; Galina V. Sukoian, ulitsa Ordzhonikidze,2, kv.12, Rustavi; Zinaida G. Khugashvili, Gldansky massiv, 4 mikroraion, korpus 101, kv. 28, Tbilisi; Dali R. Tatulashvili, plato Tsutsubidze, 4 mikroraion, korpus 16, kv. 60, Tbilisi; Evgenia V. Selikhova, prospekt Tsritsy Tamary, 18, kv. 104, Tbilisi; Nodar N. Kipshidze, ulitsa Sumbatashvili-Juzhina, 9, kv. 2, Tbilisi; Eteri I. Guchua, Digomsky massiv, 1 kvartal, korpus 11, kv.5., Tbilisi, all of Georgia

[21] Appl. No.: 495,298

[22] Filed: Jun. 28, 1995

Related U.S. Application Data

[63] Continuation of Ser. No. 228,747, Apr. 18, 1994, abandoned.

[51] Int. Cl.$^6$ .................. A61K 31/135; A61K 31/54; A61K 31/705; A61K 38/16

[52] U.S. Cl. .................. 514/26; 514/6; 514/45; 514/46; 514/225.8; 514/651

[58] Field of Search .................. 514/26, 6, 45, 514/46, 225.8, 651

[56] References Cited

PUBLICATIONS

Kostin, V. I. (Dep. Pharmacol., Med. Inst., Kemerovo 650029, USSR). Farmakol. Toksikol. (Moscow), 52(6), 49–52 (Russ) 1989.

Karsanov et al. (Repub. Res. Cent. Med. Biophys., Tbilisi, USSR), Izv. Akad. Nauk Gruz. SSR, Ser. Biol., 8(6), 393–9 (Russ) 1982.

*Primary Examiner*—Phyllis G. Spivack
*Attorney, Agent, or Firm*—Ladas & Parry

[57] ABSTRACT

The invention provides a cardiotropic formulation comprising a cardiac glycoside, a beta-adrenergic receptor stimulant nicotinamide adenine dinucleotide, cytochrome C and inosine for use in conditions of heart failure.

14 Claims, No Drawings

CARDIOTROPIC FORMULATION

This is a continuation of application(s) Ser. No. 08/228, 747 filed on Apr. 18, 1994, now abandoned.

TECHNICAL FIELD

The present invention relates to cardiology, and more particularly it relates to the preparation of cardiotropic medicaments having a potent effect in severe and refractory conditions of cardiac insufficiency.

BACKGROUND ART

Known in the are is a number of cardiotropic medicaments, in particular a pharmaceutical composition, Ildamen-novodigal (patent No. 3332 Arzneim . U.el,Forsch (Drug Res.),25,Nr.3 (1975), F. Stroman und R. Hempel. Kombination yon Oxyfedrin mit 3-acetildigoxin), which is referenced here as the prior art to a cardiotropic formulation of the invention known under trade name Refrakterin.

The Ildamen-novodigal formulation including 0.2 mg of beta-acetyldigoxin and 18 mg of oxyfedrin is in common use for treatment of a cardiac insufficiency including conditions associated with coronary circulatory failure. Depending on the severity of patient's condition a daily medication of the combination may be increased up to 0.6 mg of beta-acetyldigoxin and 36 mg of oxyfedrin, and the treatment period may be longed for 1 month. The action of the combination of beta-acetyldigoxin and oxyfedrin is based on a positive inotropic synergism. Such combination of beta-acetyldigoxin and oxyfedrin provides a considerable decrease in toxicity of the former, prevents the occurence of bradycardia and arrhythmia thereby increasing the patient's drug tolerance. However, despite wider range over curable and toxic doses of beta-acetyldigoxin combined with oxyfedrin, the gap between them is still small.

The usage of such combination may cause of intoxication, especially in cases of cardiac hypersensivity to glycosides, in patients with myocardial inflammations, particularly in patients with influenza-related or acute isolated myocarditis, and alcohol-drinker's cardiomyopathy.

The usage of beta-acetyldioxin in combination with oxyfedrin at a considerably lower dose than that of the ildamen-novodigal formulation in cardiomyocyte energy-deficient conditions, such as a well-defined heart insufficiency arising from a toxic-allergic myocarditis, may cause non-responsiveness of the myocardial contractile protein system (Tabl.2) which will aggravate the energy-deficient state of cardiac muscle cell (Tab.3).

If such compounds are used individually, the enhancement of myodynamia of contractile proteins are accompanied with a considerable rise in ATP, and yet CP (creative phosphate) decreases in content. (Tabl.3). As a consequence of the deterioration of a metabolic state, there occurs the activation of myocardial and cardiomyocyte degeneration (N. N. Kipshinidze et al., 1983, Materialy nauchnoi sessii NII klinicheskoi i eksperimentalnoi terapii Minzdrava Gruzii). This phenomenon may be considered to be the basis of cardiac refractory reaction to the conventional methods of treatment.

The object of the present invention is to provide a cardiotropic formulation, which medicative effect together with a low toxicity, will allow one to restore myocardial contractile force and increase the compensation abilities in a well-defined and severe heart failure including cardiac insufficiency with refractory reaction to the conventional methods of treatment and to cut the time for attaining positive results.

DISCLOSURE OF THE INVENTION

The object of the invention is attained by providing a formulation, hereinafter refered to as Refrakterin, distinguished from ildamen-novodigal in that it further includes nicotinamide adenine dinucleotide (NAD), cytochrome C and inosine (riboxin), with oxyfedrin and beta-acetyldigoxin presenting in smaller amounts than that of ildamen-novodigal, at the following weight ratio of ingredients:

| | |
|---|---|
| cardiac glycoside | 0.05–0.2 |
| B-adrenoceptor stimulant | 0.3–3.5 |
| nicotinamide adenine dinucleotide | 0.5–5 |
| cytochrome C | 5–15 |
| inosine (riboxin) | 20–250 |

From the results of our fundamentals follows that severe cardiac insufficiency in various heart diseases at the stage of too far progression of it and in conditions with refractory reaction occuring at myocardial inflammations, alcohol-drinker's cardiomyopathy (and probably at other cardiac diseases) substantially is associated with a simultaneous disturbance of three subcellular systems which are responsible for cardiomyocyte contraction-relaxation including the contractile proteins system, transmembrame Ca transport (coupling the excitation—contraction, regulating the power of contraction and evoking the relaxation of cardiac muscle) and the metabolizable energy system (ensuring an easily available energy source for utilization of it by all cellular systems) (Tabl.1).

Thus, to overcome the problems associated with a refractory reaction and provide a successful recovery of the power failure of the heart a homeostatic state for normal function of the three systems as mentioned above is required, since the activation of one (or two as it is the case of ildamen-novodigal) of such three systems does not cause the normalization of cardiac contractile function, and there occur refractory reaction to the preparation used. In addition, cardiomyocyte structural and functional abnormalities may occur because of the increased (non-compensable) ATP and the aggravation of energy depletion. It is precisely the picture as indicated above which is under observation in myocardial inflammations under ildamen-novodigal treatment, using even much less amounts than that of the original formulation (Tabl. 3).

Thus, the problem directed to overcoming the refractory reaction and attaining a fast, successful reparation of functional activities of the three cardiomyocyte systems is to restore a steady, equilibrium state of functioning of all the above cardiomyocyte systems which are responsible for myocardial contraction-relaxation. In this case, the adequate repair of metabolic activity (in sense of energetics) is of crucial importance, since the activation of function, both the contractile protein system and ionic pumps, give rise to a considerable increase in consumption of energy by cells. Most likely, it is the energy-deficient state which is the basis of the refractory reaction of severe heart failures to the conventional methods of treatment, wherein would take place a one-sided activation of the contractile protein system without the required stimulation of cellular energetic system.

The energy-deficient conditions in any heart disease accompanied with the development of myocardial hypoxia (myocardial infarction, inflammatory and alcoholic cardiac failures, terminal heart insufficiency and the like) are associated not only with the decrease in rate of cellular oxygen transport, and also with considerable losses of cellular cytochrome C, NAD and adenylate nucleotides.

The complex formulation including NAD, cytochrome C, inosine, a cardiac glycoside (β-acetyldigoxin or β-methyldigoxin, or strophanthin K, a contractile protein activator) and a β-adrenoceptor stimulant (oxifedrin or nonachlazin, a cardiotropic sympathomimetic) has overcome the problems associated with a refractory reaction in heart insufficiency and a fast normalization of myocardial structural and functional status.

The usage of the formulation of the invention in toxic-allergic myocarditis with a well-defined power failure of the heart provides the complete restoration (Tabl.4) of normal intracardiac or peripheral hemodynamics even under cardiac hypertension (Tabl 5) This effect is accomplished by a steady equilibrium of functioning of the three cardiomyocyte systems which are responsible for contraction-relaxation reaction. In this case, the following picture develops:

The exogeneous NAD compensates the deficiency of cytosolic and mitochondrial NAD pools. This causes the normalization of NAD-dependent glycolate dehydrogenase activities, glycolytic oxidoreduction and, in turn, ATP production through the glycolytic pathway. In addition, it restores the rate of proton translocation from cytosole to mitochondria (via the malate-aspartate shuttle) for further utilization of it in the electron transport chain.

The replacement of mitochondrial NAD deficiency activates the Krebs cycle NAD-dependent dehydrogenases and regenerates proton translocation from the tricarboxylic acid cycle to the electron transport chain.

In turn, mitochondrial exogenous cytochrome C is incorporated into (on is own place) the electron transport chain. This provides the regeneration (by volume) of electron transport to oxygen and the normal mitochondrial ATP-producing capacity in the oxidative phosphorylation associated with passing the electrons through their transport chain.

The picture described may be fully developed with the proviso that the replacements of NAD and cytochrome C take place at a time.

The replacement of NAD depletion only (by capacity) does not provide the complete restoration of energetic potential of the system since the carrying capacity of the electron transport chain is still low, and the chain is unable to cope with proton flows coming from the Krebs cycle and cytosolic component. By virtue of the action of exogenous NAD the level of CP does not increase to the normal (Tabl.6), whereas there is the tendency for a increase in ATP and a decrease in ATP/ADP ratio (Tabl.6,7).

The replacement of cytochrome C losses solely (which is in common use today) also does not provide the complete restoration of the ATP-producing capacity of the energy transfer system (Tabl.6), as the replenishment of cytochrome C losses will not cause the normalization of [NAD]/[NAD.H] ratio (Tabl.8 ) which regulates dehydrogenase activity. In this case, the ADP level goes low, and [ATP]/[ADP] ratio rises above-normal.

The replacement of losses, either NAD or cytochrome C (Tabl.8), does not cause the normalization of the total adenyl nucleotides (Tabl.6, 7). Their total content is still low.

The replacement of the total adenyl nucleotides may be attained by including inosine in the formulation, which promotes de novo adenyl nucleotide synthesis (Tabl. 9).

In addition, inosine enhances considerably the coronary circulation (oxygen delivery to cardiac muscle), and assists in liberating oxygen from oxyhemoglobin of peripheral blood. This, without any doubt, contributes significantly to the restoration of cardiomyocyte ATP-producing capacity that is a matter of great concern at the increasing heart stresses.

Thus, the introduction of exogenous NADs, cytochrome C and inosine into the composition for the replacement of endogenous NAD and cytochrome C losses, and apparently of inosine, makes it possible to restore a homeostatic state of the energy transfer system (normal levels of ATP, ADP, AMP, CP, NAD and NAD.H), its functional capacity,[ATP]/[ADP] and $$\frac{[ADP] [C] [P]}{[ATP] [CP] [ADP]},$$

as along with the absolute content of ATP, ADP, AMP, CP, NAD and NAD.H their ratios are of great importance in regulation of energetic state of the system, that is the case in hand is not a simple summation over the positive effects (each of the agents used activates ATP production to one or another degree), and it means a fine adjustment of such system. It should be noted that normal ATP and ADT are the matter of great concern for the desired structural status of contractile proteins.

In the treatment of cardiac insufficiency after restoration of normal function of the energy exchange system the next problem is to return the contraction ability of the contractile protein system (Tabl.10). This problem is solved by including a cardiac glycoside (Tabl.10) in the formulation for its direct effects on contractile proteins. The basic preparation, Refrakterin, includes β-acetyldigoxin as the cardiac glycoside.

However, in cases of heart hypersensitivity to cardiac glycosides (for example in allergic heart failures, acute isolated myocarditis) a-methyldigoxin (Refrakterin, BM) would be appropriate for use, since the specific activity of β-methyldigoxin is high as that of β-acetyldigoxin by an order of two, with their optimum concentrations being of $10^{-8}$ and $10^{-5}$ M, correspondingly (FIG. 1, Tabl.11).

In case of acute heart insufficiency associated with energy- deficient condition, strophanthin K would be suitable for use (Refrakterin, SK) as the alternative of β-acetyldigoxin because, if chosen at the optimum amount, it acts on energy transformation, both quantitatively (like β-acetyldigoxin) and qualitatively (Tabl.11,14), that is it increases the contraction efficiency. In addition, the range of effective doses for strophanthin K goes far beyond that of β-acetyldigoxin plus β-methyldigoxin. This allows such glycoside to be used effectively in the decreased amounts than that of Refrakterin (FIG. 1).

As β-methyldigoxin chosen at the optimum concentration has effects, like strophanthin K, on contractile protein-transformed energy, both quantitatively and qualitatively, Refrakterin BM is suitable in acute or chronic heart insufficiency which is followed by oxygen- and energy deficiencies.

Finally, the next problem is to provide the normal function of the Ca transport system (Tabl.13). As cardiac glycosides belonging to the foxglove class have no effects directly on the contractile protein system (strophanthin K acts on both systems) the basic formulation (Refrakterin) includes a cardiotropic β-adrenergic receptor stimulant, oxyfedrin, to normalize the function of Ca transport system. Oxyfedrin promotes the intake and release of Ca from sarcoplasmatic reticulum and brings the rate of such processes to the normal values (Tabl.14). In addition, oxyfedrin has a direct effect on the contractile protein system and accelerates glycolysis of phosphorylase due to transformation of it to its active form.

Oxyfedrin has these effects through the activation of adenylate cyclase (Tabl.14a), the inhibition of phosphodiesterase activity (Tabl.14b) and the increase in content of myocardial cAMP.

Moreover, oxyfedrin has effects on the energy-producing system by increasing the ATP level, whereas there occur a considerable decrease in CP (Tabl.3).

Alternatively, oxyfedrin may be replaced with its analogue, nonachlazin (Refrakterin H), with the dose of the latter should be at least 5 times as high as that of the former (Tabl.14 c).

Thus, each ingredient of refrakterin assists in the increase in level of ATP (up to its normal), contraction ability of the contractile protein system and rate of the cardiomyocyte transmembrane Ca transport to a greater or lesser extent. However, the end result of Refrakterin is not the sum of its specific effects, and it appears to be the case of a complex regulation of functional activities of the three cardiomyocyte systems responsible for contraction-relaxation reaction to provide the complete normalization of cardiomyocyte contractile function (even under hypertension) (Tabl.5).

The formulation of the invention is prepared as follows:
NAD (0.5 mg), cytochrome C (10 mg), inosine (80 mg), oxyfedrin (0.3 mg) and beta-acetyldigoxin (0.075) (based on kg of animal body weight) are mixed together and the resultant mixture before its direct usage, is dissolved under agitating in 6 ml of a commercially available normal saline which was heated to a temperature of 38°–40° C. The preparation was stored at 4° C. prior to dilution of it.

The present invention will become more fully apparent from the following Examples of testing the claimed preparation, Refrakterin.

Example 1

Medicative effect of Refrakterin in a 3-day TAM

Toxic and allergic myocarditis was induced in rabbits according to the methods of S. V. Andreev and M. V. Sokolov ("Sanogenesis, Meditsina, 1968) by injecting twice intravenously 2 ml of horse blood serum every forth day. Seven days after completion of the last injection 0.5 ml of staphyloccocia toxin were infused.

A medical effect of Refrakterin was recorded after administration of it within a 2-day period at a daily dose of 90.5 mg/g, beginning on the second day from the disease progression.

With a 3-day TAM the administration of Refrakterin within a 2-day period returns the normal status of a peripherial and intracardiac hemodynamics including the normalization of cardiac systolic and diastolic functions (Tabl.4) and their coordination, and the liquidation of blood congestion in lungs and liver. As this takes place, cardiomiocyte functional status will be restored so firmly that heart is capable to cope even with overloads (Tabl.5)

Example II

Medicative effect of Refrakterin in a 10-day TAM

TAM was induced according to the same procedure as disclosed for a 3-day TAM. A pharmaceutical activity of Refrakterin was recorded after administration of the preparation at a dosage of 90.875 mg/kg within a 5-day period. In these tests for an additional effect on the inflammation process the animals were treated by injection of Refrakterin to them followed by a simultaneous oral administration of acetylsalicylic acid in a dosage of 0.25 mg/kg body weight, beginning on the fifth day from the disease progression. In special experiments aspirin in such dosage has been discovered to have no marked effects on functional activity of any of the three cardiomyocyte systems which are responsible for the contraction-relaxation reaction.

The administration of Refrakterin every day within a five-day treatment period leads to the elimination of peripheral congestion (interstitial fluid in liver, lungs and heart itself decreases to the normal in content), the normalization of cardiac systolic and diastolic functions and their coordination, ensuring normal cardiac work not only at rest (Tabl.4), but under cardiac hypertension as well (Tabl.5)

The Refrakterin treatment of a 10-day TAM results in the coordinated repair of functional activities of the contractile proteins (Tabl.10) and cardiomyocyte transmembrane Ca transport (Tabl.13) with adequate promotion the rate of ATP production as an easily available energy source and energy accumulation as CP (Tabl.15), thereby causing a sharp improvement in cardiomyocyte ultrastructure. In this case it is paticularly remarkable that the restoration of the rate of contraction process and Ca transport with the metabolisable energy support takes place also under cardiac hypertension. Thus, the Refrakterin treatment provides a steady, equilibrium repair of functioning the three cardiomyocytes systems which are responsible for the contraction-relaxation reaction.

Comparative study of effects of Refrakterin and β-acetyldigoxin-oxyferdin combination The administration of beta-acetydigoxin in combination with oxyferdin even in considerably decreased amounts than that of ildamen-novodigal (0.15 mg/kg of beta-acetydigoxin+0.6 mg/kg of oxyferdin) for 2 days in both a 3-day- and 10-day TAM causes a sharp increase in myocardial tension which generates the contractile protein system (Tabl.16), with the level of adenyl nucleotides being the same as seen in Control. At the same time the CP content remains at Control level. The administration of such combination in much less amounts (0.05 mg/kg of beta-acetydigoxin +0.2 mg/kg oxyferdin) in allergic myocarditis and adrenaline-caffeine-related heart failure evokes the decrease not only in level of CP, but in ATP as well, due to rising the tension generated by the contractile proteins.

Thus, even a short-term administration of ildamen-novodigal in myocardial inflammations leads to the aggravation of cardiomyocyte energy-deficient state that may cause, eventually, the deterioration of myocardial structure due to the progression of parenchymatous degradation.

Industrial applicability

A cardiotropic formulation of the invention may be used in treatment of severe and refractory conditions of cardiac insufficiency for recovery of the power force of the heart and improvement of myocardial compensation abilities as well as the cutting of time for attaining positive pharmacologic effect.

TABLE 1

State in Systems of Contractile Proteins, Energy Supply and Ca$^{2+}$ transport in a 10-day TAM

Mechanical parameters of contraction

| Ventricle | Parameter | Normal (n = 16) | TAM (n = 13) |
|---|---|---|---|
| Left | Tension, mH/mm$^2$ | 2.48 ± 0.18 | 1.57 ± 0.13*** |
|  | Work, nJ/mm$^3$ | 21.4 ± 3.0 | 9.0 ± 2.0** |
| Right | Tension, mH/mm$^2$ | 2.44 ± 0.20 | 1.55 ± 0.15** |
|  | Work, nJ/mm$^3$ | 19.9 ± 3.0 | 8.3 ± 2.0* |

Levels of Adenyl nucleotides and creatine phosphate (CP)

| Ventricle | Group | ATP | ADP | ATP + ADP + AMP | ATP/ADP | Energetic potential | CP |
|---|---|---|---|---|---|---|---|
| Left | Normal | 2.50 ± 0.13** | 2.02 ± 0.12* | 5.59 ± 0.18*** | 1.35 ± 0.12 | 0.65 ± 0.02 | 3.40 ± 0.18*** |
|  | TAM | 1.30 ± 0.13 | 1.49 ± 0.15 | 3.56 ± 0.21 | 1.05 ± 0.12 | 0.57 ± 0.02 | 1.52 ± 0.07 |
| Right | Normal | 2.40 ± 0.13*** | 1.84 ± 0.10 | 5.25 ± 0.22*** | 1.43 ± 0.13 | 0.65 ± 0.01 | 3.26 ± 0.11 |
|  | TAM | 1.67 ± 0.12 | 1.51 ± 0.18 | 3.77 ± 0.34 | 1.27 ± 0.10 | 0.60 ± 0.19 | 1.45 ± 0.10 |

$^{45}$Ca$^{2+}$ Binding, Intake and Release from CPF, Mitochondrial Ca Uptake and Ca Content in CPF, mitochodria and cardiac muscle in TAM (nmole $^{45}$Ca$^{+2}$ per g protein)

| Test | Ca binding, 1 min. | Ca uptake, min. 3 | 5 | 10 | 15 | 25 | 35 | 45 | Release Ca uptake | Ca released |
|---|---|---|---|---|---|---|---|---|---|---|
| Normal (n = 15) | 43.5 ± 0.9 | 834 ± 50*** | 945 ± 37*** | 1171 ± 43*** | 1297 ± 27*** | 1356 ± 22*** | 1426 ± 23*** | 1414 ± 19*** | 1345 ± 29*** | 276 ± 21** |
| 10-day TAM (n = 7) | 29.4 ± 0.9 | 563 ± 25 | 608 ± 128 | 698 ± 38 | 780 ± 39 | 829 ± 15 | 905 ± 36 | 908 ± 23 | 938 ± 35 | 155 ± 28 |

| Test | Mytochondria Uptake, min. 5 | 15 | 30 | CPF mcM | Mitochondria content Ca per g protein | Cardiac muscle Ca per g tissue |
|---|---|---|---|---|---|---|
| Normal (n = 15) | 116 ± 9.0* | 188 ± 5.7** | 210 ± 7.0 | 49.0 ± 4.0*** | 50.0 ± 7.5 | 2.5 ± 0.5* |
| 10-day TAM (n = 7) | 159 ± 19 | 258 ± 23 | 240 ± 8 | 28.2 ± 1.2 | 33.0 ± 3.5 | 1.12 ± 0.2 |

TABLE 2

Effects of oxyfedrin (0.6 mg/kg), beta-acetyldigoxin (0.15 mg/kg) and combinations thereof on left/right ventricle tension in a 10-day TAM (mH/mm$^2$)

| Group, Subgroup | | Vetricle Left | Right |
|---|---|---|---|
| Normal (n = 27) | 1 | 2.1 ± 0.11 | 1.98 ± 0.14$^x$ |
| 10-day TAM |  |  |  |
| Control (n = 9) | 2 | 0.95 ± 0.15 | 0.88 ± 0.14** |
| TREATMENT |  |  |  |
| Oxyfedrin (n = 5) | 3 | 4.2 ± 0.49 | 3.90 ± 0.42 |
| b-Acetyldigoxin (n = 3) | 4 | 4.3 ± 0.48 | 3.8 ± 0.19 |
| Oxyfedrin + b-Acetyldigoxin (n = 3) | 5 | 4.93 ± 0.4 | 4.7 ± 0.37 |

TABLE 2-continued

Effects of oxyfedrin (0.6 mg/kg), beta-acetyldigoxin (0.15 mg/kg) and combinations thereof on left/right ventricle tension in a 10-day TAM (mH/mm$^2$)

| Group, Subgroup | | Vetricle Left | Right |
|---|---|---|---|
| Least significant difference between groups (P) | 1-2 | <0.001 | <0.001 |
|  | 1-3 | <0.001 | <0.001 |
|  | 1-4 | <0.001 | <0.001 |
|  | 1-5 | <0.001 | <0.001 |
|  | 2-3 | <0.001 | <0.001 |
|  | 2-4 | <0.001 | <0.001 |
|  | 2-5 | <0.001 | <0.001 |
|  | 3-4 | — | — |
|  | 3-5 | — | — |
|  | 4-5 | — | — |

$^x$n = 24
**n = 8

TABLE 3

Levels of adenyl nucleotides and creatine phosphate in allergic myocarditis under effect oxyfedrin (0.6 mg/kg) b-acetyldigoxin (0.15 mg/kg) and combination thereof (μM per g wet tissue)

| Group | ATP | ADP | AMP | CP |
|---|---|---|---|---|
| Normal n = 8 | 2.38 ± 0.14 | 1.92 ± 0.46 | 0.92 ± 0.11 | 1.08 ± 0.08+ |
| Control 10-day TAM n = 10 | 1.67 ± 0.15* | 1.80 ± 0.14 | 0.84 ± 0.37 | 0.59 ± 0.09* |
| Oxy-fedrin* n = 7 | 2.28 ± 0.39 | 2.39 ± 0.27 | 1.73 ± 0.11 | 0.29 ± 0.01*x |
| b-Acetyl-digoxin n = 5 | 2.28 ± 0.15x | 2.95 ± 0.56 | 1.24 ± 0.31 | 0.41 ± 0.11* |
| Oxy-fedrin + b-acetyl-digoxin n = 4 | 1.63 ± 0.37 | 2.30 ± 0.61 | 1.15 ± 0.34 | 0.22 ± 0.04*x |

Note:
+n = 12, comparison to: normal-*, Control-x
+e,crc *oxyfedrin+ee - 1-propanone-[3-(2-hydroxy-1-methyl-2-phenyl-ethyl)amino]-1-(3-methoxyphenyl)

TABLE 4

Intracardiac hemodynamics in TAM after Refrakterin treatment

| Group | Heart rate, b/min. | LVP, mmHg | dp/dt max mmHg/s | EDP, mmHg/s | dp/dt min mmHg/s | Veragood CI, $s^{-1}$ | CEI by dp/dt max mmHg/s × g | CWI, mmHg × b/s / g |
|---|---|---|---|---|---|---|---|---|
| Normal (n = 5) | 228 ± 15 | 71 ± 9 | 1240 ± 306 | 7 ± 2 | 1313 ± 281 | 21.1 ± 5.0 | 547 ± 93 | 6679 ± 1365 |
| TAM CONTROL | | | | | | | | |
| 3-day n = 3 | 240 ± 29 | 81 ± 9 | 1006 ± 122 | 15 ± 4 | 720 ± 95* | 15.8 ± 3.9 | 439 ± 65 | 4685 ± 203* |
| 10-day n = 4 | 202 ± 14 | 49 ± 8*x | 1017 ± 174 | 27 ± 8*x | 533 ± 105* | 15.4 ± 1.8 | 409 ± 58* | 3828 ± 989x+ |
| Refrakterin treatment | | | | | | | | |
| 2 day n = 4 | 218 ± 15 | 84 ± 10x+ | 1300 ± 210 | 8 ± 2*x | 1180 ± 115 | 20.8 ± 1.6 | 583 ± 45x+ | 6038 ± 979x+ |
| 5 day n = 7 | 244 ± 8 | 69 ± 10x+ | 1280 ± 366 | 5 ± 2x+ | 1033 ± 28*x | 21.5 ± 5.4 | 637 ± 186+ | 7378 ± 1020x+ |

Note:
Comparison to: normal-*; 3-day TAM-x; 10-day TAM-+
*Treatment time: 2 day in 3-day TAM, 5 day in 10-day TAM

TABLE 5

Intracardiac hemodynamics in TAM after Refrakterin treatment under hypertension

| Group | Heart rate, b/min. | EDP, mmHg/ss | LVP, mmHg | dp/dt, max mmHg/s | Veragood CI, $s^{-1}$ | CEI by dp/dt mmHg s × g | CWI, mmHg × b/s | dp/dt max mmHg/s max |
|---|---|---|---|---|---|---|---|---|
| Normal n = 5 | 192 ± 15 | 12 ± 26 | 112 ± 23 | 1264 ± 504 | 18 ± 3 | 558 ± 85 | 7010 ± 966 | 953 ± 193 |
| TAM CONTROL | | | | | | | | |
| 3-day n = 3 | 210 ± 14 | 27 ± 8* | 133 ± 14 | 1650 ± 27 | 16 ± 4 | 702 ± 92 | 8277 ± 404 | 1289 ± 163* |
| 10-day n = 4 | 218 ± 19 | 31 ± 2* | 141 ± 20 | 1595 ± 10 | 13 ± 2* | 858 ± 255 | 8333 ± 2621 | 767 ± 436* |
| Refrakterin treatment | | | | | | | | |
| 2 day n = 4 | 200 ± 25 | 16 ± 4x+ | 111 ± 13 | 1358 ± 110 | 15 ± 3 | 1360 ± 380 | 8010 ± 1050 | 980 ± 85x |

TABLE 5-continued

Intracardiac hemodynamics in TAM after Refrakterin treatment under hypertension

| Group | Heart rate, b/min. | EDP, mmHg/ss | LVP, mmHg | dp/dt, max mmHg/s | Veragood Cl, $s^{-1}$ | CEI by dp/dt mmHg s × g | CWI, mmHg × b/s | dp/dt max mmHg/s max |
|---|---|---|---|---|---|---|---|---|
| 5 day n = 7 | 193 ± 23 | 18 ± 4[+] | 109 ± 15[+] | 1452 ± 269 | 14 ± 2 | 1766 ± 1103 | 8230 ± 1820 | 1004 ± 177[+] |

Note:
Comparison to: normal-*; 3-day TAM-[x]; 10-day TAM-[+]
*Treatment time: 2 day in 3-day TAM, 5 day in 10-day TAM

TABLE 6

Levels of adenyl nucleotides and CP (mcM/g wet tissue) in myocardial left ventricle in rabbits with a 10-day allergic myocarditis after treatment with NAD and cytochrome C

| Group | ATP | ADP | AMP | ATP + ADP + AMP | ATP/ADP | Energy potential | CP |
|---|---|---|---|---|---|---|---|
| Norm (n = 25) | 2.5 ± 0.13 | 2.02 ± 0.12 | 1.07 ± 0.07 | 5.52 ± 0.18 | 1.35 ± 0.07 | 0.65 ± 0.02 | 3.40 ± 0.18 |
| MYOCARDITIS | | | | | | | |
| Control (n = 20) | 1.3 ± 0.13*** | 1.49 ± 0.16** | 0.78 ± 0.09*** | 3.56 ± 0.21*** | 1.05 ± 0.12* | 0.57 ± 0.01*** | 1.52 ± 0.07*** |
| TREATMENT | | | | | | | |
| NAD 0.05 mg/kg (n = 12) | 2.43 ± 0.22[+++] | 2.68 ± 0.33**[++] | 0.58 ± 0.14** | 5.57 ± 0.51[++] | 1.14 ± 0.22 | 0.65 ± 0.04[+] | 1.50 ± 0.12*** |
| Cytochrome C 5 mg/kg (n = 9) | 2.19 ± 0.09[+++] | 1.42 ± 0.05***[xx] | 0.62 ± 0.09*** | 4.24 ± 0.16***[+] | 1.56 ± 0.09[++] | 0.69 ± 0.02[+++] | 2.07 ± 0.22***[+x] |

Note:
the same symbols as given in Table 2 are used

TABLE 7

Effects of medication of NAD (0.05 mg/kg) and cytochrome C (10/kg) on myocardial right-ventricular adenyl nucleotides in rabbits with a 3-day allergic myocarditis (mcM/g wet tissue)

| Group, Subgroup | | Statictical values | ATP | ADP | AMP | ATP/ADP | Total Nucleotides | Energetic Potential |
|---|---|---|---|---|---|---|---|---|
| Normal (n = 25) | 1 | X ± $m_{\bar{x}}$ | 2.40 ± 0.13 | 1.84 ± 0.10 | 0.99 ± 0.07 | 1.43 ± 0.13 | 5.25 ± 0.22 | 0.65 ± 0.01 |
| MYOCARDITIS | | | | | | | | |
| Myocarditis (n = 11) | 2 | X ± $m_{\bar{x}}$ | 1.55 ± 0.10 | 1.45 ± 0.19 | 0.83 ± 0.13 | 1.27 ± 0.17 | 3.88 ± 0.33 | 0.60 ± 0.02 |
| TREATMENT | | | | | | | | |
| NAD (n = 11) | 3 | X ± $m_{\bar{x}}$ | 2.06 ± 0.12 | 1.99 ± 0.13 | 0.60 ± 0.03 | 1.07 ± 0.11 | 4.73 ± 0.42 | 0.63 ± 0.02 |
| Cytochrome C (n = 8) | 4 | X ± $m_{\bar{x}}$ | 2.00 ± 0.28 | 1.09 ± 0.15 | 0.63 ± 0.17 | 2.14 ± 0.28 | 3.82 ± 0.42 | 0.66 ± 0.05 |
| | | $P_{1-2}$ | 0.001 | — | — | — | 0.001 | 0.05 |
| | | $P_{1-3}$ | — | — | 0.001 | — | — | — |
| | | $P_{1-4}$ | — | — | 0.05 | — | — | — |
| | | $P_{2-3}$ | 0.01 | 0.05 | — | — | — | — |
| | | $P_{2-4}$ | — | — | — | 0.05 | — | — |
| | | $P_{3-4}$ | — | 0.01 | — | 0.01 | — | — |

TABLE 8

Levels of NAD and NAD-H in myocardial left ventricle in a 10-day TAM after treatment with NAD (0.5 mg/kg) and cytochrome C (5 mg/kg) (mcM/g of wet tissue)

| Groups, Subgroups | NAD | NAD-H | Total | NAD-H/NAD |
|---|---|---|---|---|
| NORMAL (n = 8) | 0.68 ± 0.02 | 0.36 ± 0.04 | 1.08 ± 0.03 | 0.50 ± 0.036 |
| TAM | | | | |
| Control (n = 8) | 0.47 ± 0.05*** | 0.41 ± 0.05 | 0.84 ± 0.03*** | 0.86 ± 0.04*** |
| TREATMENT | | | | |
| NAD 0.5 mg/kg | 0.68 ± 0.04+++ | 0.33 ± 0.015 | 1.03 ± 0.03+++ | 0.46 ± 0.04+++ |
| Cytochome C 5 mg/kg (n = 6) | 0.54 ± 0.04**x | 0.48 ± 0.09 | 1.05 ± 0.07+ | 0.90 ± 0.08xxx |

Comparison to: normal-\*; control-+; NAD medication in combination with cytochrome C-x
No symbol - not statistically significant.
One symbol - $P < 0.05$; two symbols - $P < 0.01$; three symbols - $P < 0.001$

TABLE 9

Levels of rabbit cardiac adenyl nucleotides in experimental 10-day TAM under effect inosine

| | | Left ventricle | | | | | | Right ventricle | | | | |
|---|---|---|---|---|---|---|---|---|---|---|---|---|
| | | mcM/g wet tissue | | | Energetic | AdT/ | mcM/g wet tissue | | | | Energetic | AdT/ |
| GROUP | | AdT | ADP | AMP | Total | potential | ADP | ATP | ADP | AMP | Total | potential | ADP |
| Normal (n = 1) | 1 | 3.23 ± 0.09 | 1.49 ± 0.09 | 0.71 ± 0.13 | 5.36 ± 0.12 | 0.73 ± 0.02 | 2.23 ± 0.18 | 2.75 ± 0.26 | 1.47 ± 0.17 | 0.74 ± 0.03 | 4.89 ± 0.43 | 0.68 ± 0.02 | 1.86 ± 0.18 |
| MYO-CARDITIS | | | | | | | | | | | | | |
| Control (n = 7) Inosine therapy | 2 | 1.51 ± 0.09 | 1.27 ± 0.13 | 0.69 ± 0.08 | 3.48 ± 0.20 | 0.62 ± 0.02 | 1.26 ± 0.13 | 1.33 ± 0.12 | 1.24 ± 0.16 | 0.73 ± 0.05 | 3.29 ± 0.26 | 0.59 ± 0.01 | 1.15 ± 0.09 |
| 80 mg/kg (n = 6) | 3 | 2.66 ± 0.13 | 1.50 ± 0.10 | 0.99 ± 0.05 | 5.14 ± 0.17 | 0.66 ± 0.01 | 1.82 ± 0.18 | 2.25 ± 0.43 | 1.74 ± 0.21 | 0.63 ± 0.08 | 4.82 ± 0.29 | 0.65 ± 0.01 | 1.41 ± 0.21 |
| 160 mg/kg | 4 | 2.99 ± 0.11 | 2.36 ± 0.15 | 0.98 ± 0.16 | 6.20 ± 0.31 | 0.65 ± 0.0 | 1.25 ± 0.12 | 2.23 ± 0.20 | 1.85 ± 0.25 | 0.96 ± 0.06 | 0.96 ± 0.23 | 0.63 ± 0.02 | 1.39 ± 0.30 |
| Least significant difference between groups (P) | $P_{1-2}$ | <0.001 | — | — | 0.001 | 0.001 | 0.001 | 0.001 | — | — | — | 0.01 | 0.05 |
| | $P_{2-3}$ | <0.001 | — | 0.01 | 0.001 | — | 0.05 | 0.001 | — | — | — | 0.01 | — |
| | $P_{2-4}$ | <0.001 | 0.001 | — | 0.001 | — | — | 0.01 | — | 0.05 | 0.01 | 0.001 | — |
| | $P_{1-3}$ | <— | 0.001 | — | 0.02 | — | 0.02 | — | — | — | — | — | — |
| | $P_{1-4}$ | <0.01 | — | — | — | — | — | — | — | — | — | — | — |
| | $P_{3-4}$ | <— | 0.001 | — | 0.02 | — | 0.001 | — | — | — | — | — | — |

TABLE 10

Effect of Refrakterin on left-ventricular tension generated by PGVM in a 10-day TAM

| Group, subgroup | | Statictical index | Tension, mH/mm² |
|---|---|---|---|
| Normal TAM | 1 | M ± m$_{\bar{x}}$ | 2.39 ± 0.34 |
| Control | 2 | M ± m$_{\bar{x}}$ | 1.37 ± 0.15 |
| Refrakterin treatment | 3 | M ± m$_{\bar{x}}$ | 2.31 ± 0.26 |
| | | $P_{1-2}$ | 0.05 |
| | | $P_{1-3}$ | — |
| | | $P_{2-3}$ | 0.05 |

TABLE 11

Effects of cardiac glycosides on contraction ability and energy metabolism of normal myocardial contractile proteins

| Cardiac glycoside | P | ΔG | P/ΔG | (ΔH − ΔQ)/ΔH | ΔQ |
|---|---|---|---|---|---|
| b-Acetyldigoxin $10^{-6}$M | 136.5 | 155 | 90.2 | 95.6 | 102 |
| b-Methyldigoxin | | | | | |
| $10^{-8}$M | 168.8 | 133.9 | 189.4 | 112.6 | 98.5 |
| $10^{-6}$M | 154.6 | 86.9 | 142.1 | 88.2 | 100 |
| Strophanthin | | | | | |
| $10^{-6}$M | 168.8 | 150.5 | 131.7 | 117.6 | 110.2 |
| $10^{-8}$M | 149.8 | 83.0 | 142.1 | 90.3 | 95.6 |

Note:
given is percentil to Control (no glycosides) in the Table.

TABLE 12

Effects of cardiac glycosides on mechnical and thermodynamic contraction parameters in TAM

| Cardiac glycoside | P | ΔH | ΔH − ΔQ/ΔH |
|---|---|---|---|
| Control (10-day TAM) | 43.4 | 52.5 | 77.9 |
| b-Acetyldigoxin $10^{-6}$M | 75.6 | 63.0 | 76.2 |
| Strophanthin K $10^{-6}$M | 75.6 | 65.7 | 94.1 |

Note:
given is percentil to Control (normal) in the Table.

TABLE 13

Effect of Refrakterin on contractile protein fiblil/mitochondrial $Ca^{2+}$ transport in treatment of rabbit TAM (mcmole Ca per g protein

| Group | | Statistical index | Ca binding to CPF 1 min. | CPF 3 min. | $Ca^{2+}$ uptake | | | | CPF Ca release | | Mitochrondrial $Ca^{2+}$ uptake | | |
|---|---|---|---|---|---|---|---|---|---|---|---|---|---|
| | | | | | 15 min. | 35 min. | 45 min. | | load | release | 5 min. | 15 min. | 30 min. |
| Normal 10-day TAM | 1 | $X \pm m_{\bar{x}}$ | 43.5 1.9 15 | 834 50 15 | 1298 37 15 | 1426 23 15 | 1414 19 15 | | 1345 29 15 | 276 21 15 | 122 11 15 | 196 8 15 | 210 8 15 |
| Control | 2 | $X \pm m_{\bar{x}}$ | 29.4 0.9 10 | 563 25 7 | 780 39 7 | 905 37 7 | 908 23 7 | | 938 35 7 | 155 28 7 | 171 17 9 | 268 22 9 | 269 18 9 |
| Refrakterin treatment | 3 | $X \pm m_{\bar{x}}$ | 40.4 2.1 5 | 855 99 6 | 1473 142 6 | 1495 149 5 | 1449 152 6 | | 1382 167 5 | 226 18 5 | 140 18 5 | 249 41 5 | 235 21 5 |
| | $P_{1-2}$ | | 0.001 | 0.01 | 0.001 | 0.001 | 0.001 | | 0.001 | 0.03 | 0.01 | 0.01 | 0.01 |
| | $P_{1-3}$ | | — | — | — | — | — | | — | — | — | — | — |
| | $P_{2-3}$ | | 0.001 | 0.01 | 0.001 | 0.01 | 0.01 | | 0.01 | — | — | — | — |

TABLE 14

Myocardial CPF $Ca^{2+}$ transport in rabbit TAM after oxyfedrin treatment (mcmole Ca per g protein)

| Group | | $Ca^{2+}$ uptake | | | | | Ca release |
|---|---|---|---|---|---|---|---|
| | | 3 min. | 5 min. | 15 min. | 35 min. | 45 min. | 2 min. |
| Normal 10-day TAM | M ± m | 834 ± 50 (15) | 945 ± 37 (15) | 1297 ± 27 (15) | 1426 ± 23 (15) | 1414 ± 19 (15) | 276 ± 21 (15) |
| Control TREATMENT | M ± m | 563 ± 25 (7) | 608 ± 128 (7) | 780 ± 39 (7) | 905 ± 36 (7) | 908 ± 23 (7) | 155 ± 28 (7) |
| | P | 0.001 | 0.001 | 0.001 | 0.001 | 0.001 | 0.01 |
| Oxyfedrin 0.6 mg/kg | M ± m | 1058 ± 97 (5) | 1108 ± 74 (5) | 1319 ± 61 (5) | 1424 ± 42 (6) | 1438 ± 44 (6) | 332 ± 36 (6) |
| | P | — | — | — | — | — | — |
| | P* | 0.001 | 0.001 | 0.001 | 0.001 | 0.001 | 0.001 |

P - comparisom to normal, P* - comparison to Control

TABLE 14a

Effects of nonachlazin and oxyfedrin on cardiac AC activity

Activity, pcmole cAMP/mg protein/min.

| Test conditions | Basal | Nonachlazin $10^{-6}$M | Nonachlazin $10^{-4}$M | Oxyfedrine $10^{-6}$M | Oxyfedrine $10^{-4}$M |
|---|---|---|---|---|---|
| Prior to preincubation n = 4 | 142 ± 2 | — | — | — | — |
| After preincubation n = 4 | — | 175 ± 3* | 162 ± 10 | 200 ± 15* | 189 ± 9 | n - number of recurrences
Comparison to: basal activity (*) one symbol is $P < 0.05$, two symbols - $P < 0.01$, three symbols - $P < 0.001$

TABLE 14b

Effects of nonachlazin and oxyfedrin on cardiac PDE activity

Activity, pcmole cAMP/mg protein/min.

| Test conditions | Basal | Nonachlazin $10^{-6}$M | Nonachlazin $10^{-4}$M | Oxyfedrin $10^{-6}$M | Oxyfedrin $10^{-4}$M |
|---|---|---|---|---|---|
| Prior to preincubation n = 4 | 744 ± 71 | — | — | — | — |
| After preincubation n = 5 | — | 526 ± 47 | 408 ± 24* | 543 ± 59* | 402 ± 26* | n - number of recurrences
Comparison to: original activity (*) one symbol is $P < 0.05$, two symbols - $P < 0.01$, three symbols - $P < 0.001$

TABLE 14c

Effects of nonachlazin and oxyfedrin on myocardial cAMP level in normal rabbit and with TAM

| Group | Medicinal agent | | cAMP, pcmole/mg protein |
|---|---|---|---|
| Control | n = 5 | 1 | 9.5 ± 0.06 |
|  | Nonachalazin n = 4 | 2 | 12.5 ± 0.07 |
|  | Oxyfedrin n = 4 | 3 | 14.3 ± 0.4* |
| 10-day TAM | n = 4 | 4 | 3.4 ± 0.2 |
|  | Nonachlazin n = 4 | 5 | 13.4 ± 0.3+++ |
|  | Oxyfedrin n = 4 | 6 | 12.0 ± 0.4+++o | n - number of recurrences
*least significant difference between 1-2 and 1-3
+least significant difference between 4-5 and 4-6
°least significant difference between 1-2 and 1-3
One symbol is $P < 0.05$, two symbols - $P < 0.01$, three symbols - $P < 0.001$

TABLE 15

Effects of Refrakterin on levels of adenyl nucleotides and CP in a 10-day TAM, (μcM/g wet tissue)

| Group, subgroup | Statistic value | | ATP | ADP | AMP | Pn | ATP/ADP | Total nucleotides | Energetic potential | Phosphorylation index | CP | Creatine |
|---|---|---|---|---|---|---|---|---|---|---|---|---|
| Normal | 1 | M ± m | 3.11 | 2.1 | 0.67 | 2.21 | 1.5 | 5.88 | 0.71 | 1.48 | 3.26 | 15.5 |
| | | | 0.18 | 0.44 | 0.10 | 0.19 | 0.09 | 0.41 | 0.014 | 0.21 | 0.14 | 1.9 |
| | | | 6 | 6 | 6 | 5 | 6 | 6 | 6 | 5 | 6 | 5 |
| TAM | | | | | | | | | | | | |
| Control | 2 | M ± m | 1.82 | 1.57 | 0.84 | 2.26 | 1.1 | 4.24 | 0.61 | 2.1 | 1.69 | 19.3 |
| | | | 0.07 | 0.07 | 0.032 | 0.07 | 0.08 | 0.08 | 0.008 | 0.37 | 0.23 | 2.31 |
| | | | 9 | 9 | 9 | 5 | 9 | 9 | 9 | 5 | 7 | 4 |
| Refrakterin treatment | 3 | M ± m | 3.13 | 2.4 | 0.74 | 2.13 | 1.43 | 6.32 | 0.58 | 1.56 | 3.12 | 18.22 |
| | | | 0.08 | 0.14 | 0.072 | 0.15 | 0.07 | 0.21 | 0.006 | 0.17 | 0.009 | 0.77 |
| | | | 11 | 11 | 11 | 7 | 11 | 11 | 11 | 7 | 7 | 6 |
| | | $P_{1-2}$ | 0.001 | 0.01 | — | — | 0.01 | 0.001 | 0.001 | — | 0.001 | — |
| | | $P_{1-3}$ | — | — | — | — | — | — | — | — | 0.001 | — |
| | | $P_{2-3}$ | 0.001 | 0.001 | — | — | 0.05 | 0.001 | 0.001 | — | — | — |

TABLE 16

Comparison of Refrakterin effectiveness to Ildamen-novodigal

| | Ingredients | Control 10-day TAM | REFRAKTERIN | | | | Prior art, Ildamen + Novodigal | | |
|---|---|---|---|---|---|---|---|---|---|
| | | | | MI | | SK | | | |
| Nicotinamide adenine dinunucleotide (NAD) | | — | 0.25 | 0.5 | 0.5 | 5 | 5 | — | — | — |
| Cytochrome C | | — | 5 | 10 | 10 | 10 | 15 | — | — | — |
| Inosine | | — | 20 | 80 | 80 | 80 | 250 | — | — | — |
| Cardiac glycoside | b-Acetyldigoxin | — | 0.05 | 0.08 | — | — | 0.2 | 0.08 | 0.15 | 0.2 |
| | b-methyldigoxin | — | — | — | 0.008 | — | — | — | — | — |
| | Strophanthin K | — | — | — | — | 0.03 | — | — | — | — |
| b-Adrenoceptor stimulant | Oxyfedrin | — | 0.3 | — | 0.3 | — | 0.3 | 0.3 | 2.0 | — | 0.3 | 0.6 | 2.0 |
| | Nonachlazin* | — | — | 1 | — | 1 | — | — | — | 3.5 | — | — | — |
| Effect on the contractile protein system | Myocardial myofibril tension | 50 | 109 | 109.5 | 108.9 | 112.6 | 126 | 121 | 155 | 239 |
| Effect on Ca transport | CPF Ca binding | 67.6 | | 92.9 | | | | 90 | 92.6 | |
| | CPF Ca uptake | 69.8 | 84.7 | 102.5 | | | 101.7 | 101 | 106.9 | |
| | CPF Ca release | 56.0 | | 81.9 | | | | 110 | 116.7 | |
| | Mitochondrial Ca uptake | 128 | | 111.9 | | | 96.2 | 58 | | |
| Effect on energy exchange | ATP | 58.5 | 95 | 100.6 | — | | 95.5 | 88.6 | 52.2 | 69.1 |
| | ADP | 74.8 | 89 | 114.3 | — | | 125.4 | 76.2 | 86.3 | 119.8 |
| | AMP | 125.4 | 91 | 110.4 | — | | 120 | 60.0 | 26.3 | 121.1 |
| | ATP/ADP | 73.3 | 82 | 88.7 | — | | 100 | | | |
| | CP | 51.8 | 98 | 95.7 | — | | 96.4 | 58.3 | | |
| | NADH/NAD | 172 | 125 | 92.0 | — | | 105.2 | | | |

Note:
*-Nonachlazin-10{b-[1,4-diazobicyclo(4,3,0)nonanyl-4-propionyl]}-2-chlorophenazine dihydrochloride

We claim:

1. An improved cardiotropic composition containing a cardiac glycoside and β-adrenergic receptor stimulant wherein the improvement comprises the inclusion of nicotinamide adenine dinucleotide, cytochrome C and inosine, wherein the composition comprises by parts by weight:

| | |
|---|---|
| cardiac glycoside | 0.05–0.2 |
| β-adrenergic receptor stimulant selected from oxyfedrine and nonachlazin | 0.3–3.5 |
| nicotinamide adenine dinucleotide | 0.5–5 |
| cytochrome C | 5–15 |
| inosine | 20–250, | and pharmaceutically acceptable carriers and diluents.

2. A cardiotropic composition according to claim 1, wherein the cardiac glycoside is β-acetyldigoxin in an amount of from 0.05 to 0.2 parts by weight.

3. A cardiotropic composition according to claim 1, wherein the cardiac glycoside is β-methyldigoxin in an amount of from 0.05 to 0.15 parts by weight.

4. A cardiotropic composition according to claim 1, wherein the cardiac glycoside is strophanthin K in an amount of from 0.05 to 0.2 parts by weight.

5. A cardiotropic composition according to claim 1, wherein the β-adrenergic receptor stimulant is oxyfedrin in an amount of from 0.3 to 2.0 parts by weight.

6. A cardiotropic composition according to claim 1, wherein the β-adrenergic receptor stimulant is nonachlazin in an amount of from 1 to 3.5 parts by weight.

7. A cardiotropic formulation comprising a cardiac glycoside selected from the group consisting of β-acetyldigoxin, β-methyldigoxin and strophanthin K; a β-adrenergic receptor stimulant selected from the group consisting of oxyfedrin and nonachlazin; nicotinamide adenine dinucleotide; cytochrome C and inosine, wherein the composition comprises by parts by weight;

| | |
|---|---|
| cardiac glycoside | 0.05–0.2 |
| β-adrenergic receptor stimulant | 0.3–3.5 |
| nicotinamide adenine dinucleotide | 0.5–5 |
| cytochrome C | 5–15 |
| inosine | 20–250 | and pharmaceutically accepted carriers and diluents.

8. A method for simultaneous restoration of ATP production, transmembrane calcium transport and the cardiomyocyte contraction—relocation system which comprises administering to a patient suffering from disruption of one or more of these mechanisms a dose effective to restore said mechanisms of a composition comprising:

a cardiac glycoside a β-adrenergic receptor stimulant, nicotinamide adenine dinucleotide, cytochrome C and inosine, wherein the composition comprises by parts by weight:

| | |
|---|---|
| cardiac glycoside | 0.05–0.2 |
| β-adrenergic receptor stimulant selected from oxyfedrine and nonachlazin | 0.3–3.5 |
| nicotinamide adenine dinucleotide | 0.5–5 |
| cytochrome C | 5–15 |
| inosine | 20–250, | and pharmaceutically acceptable carriers and diluents.

9. A method according to claim 8, wherein the cardiac glycoside is β-acetyldigoxin in an amount of from 0.05 to 0.2 parts by weight.

10. A method according to claim 8, wherein the cardiac glycoside is β-methyldigoxin in an amount of from 0.05 to 0.15 parts by weight.

11. A method according to claim 8, wherein the cardiac glycoside is strophanthin K in an amount of from 0.05 to 0.2 parts by weight.

12. A method according to claim 8, wherein the βadrenergic receptor stimulant is oxyfedrin in an amount of from 0.3 to 2.0 parts by weight.

13. A method according to claim 8, wherein the β-adrenergic receptor stimulant is nonachalzin in an amount of from 1 to 3.5 parts by weight.

14. A method according to claim 8 wherein the composition used comprises a cardiac glycoside selected from the group consisting of β-acetyldigoxin, β-methyldigoxin and strophanthin K; a β-adrenergic receptor stimulant selected from the group consisting of oxyfederin and nonachlizin; nicotinamide adenine dinucleotide; cytochrome C and inosine, wherein the composition comprises by parts by weight;

| | |
|---|---|
| cardiac glycoside | 0.05–0.2 |
| β-adrenergic receptor stimulant | 0.3–3.5 |
| nicotinamide adenine dinucleotide | 0.5–5 |
| cytochrome C | 5–15 |
| inosine | 20–250 | and pharmaceutically acceptable carriers and diluents.

* * * * *